United States Patent [19]

Kortright et al.

[11] Patent Number: 4,708,930

[45] Date of Patent: Nov. 24, 1987

[54] MONOCLONAL ANTIBODY TO A HUMAN CARCINOMA TUMOR ASSOCIATED ANTIGEN

[75] Inventors: Kenneth H. Kortright, Cooper City; David E. Hofheinz, Homestead, both of Fla.

[73] Assignee: Coulter Corporation, Hialeah, Fla.

[21] Appl. No.: 702,059

[22] Filed: Feb. 15, 1985

Related U.S. Application Data

[63] Continuation-in-part of Ser. No. 670,328, Nov. 9, 1984, abandoned.

[51] Int. Cl.$^4$ .................. G01N 33/577; G01N 33/574; G01N 33/541; G01N 33/546; A61K 49/00; C12N 5/00; C07K 15/04

[52] U.S. Cl. .................................... 435/7; 435/28; 435/29; 435/68; 435/70; 435/172.2; 435/240; 435/241; 435/188; 435/948; 530/387; 436/513; 436/518; 436/533; 436/536; 436/540; 436/542; 436/548; 436/813; 424/1.1; 424/9; 424/85; 935/95; 935/104; 935/107; 935/110

[58] Field of Search .................. 260/112 R; 514/2, 8, 514/885; 424/1.1, 9, 85, 177; 435/4, 7, 28, 29, 68, 70, 172.2, 240, 948, 241, 188; 935/95, 102–104, 106, 107, 108, 110; 436/501, 504, 513, 518, 528–534, 536, 540, 548, 800, 801, 804, 813, 815, 821; 530/387, 388

[56] References Cited

U.S. PATENT DOCUMENTS

| | | | |
|---|---|---|---|
| 4,172,124 | 10/1979 | Koprowski | 424/85 |
| 4,323,546 | 4/1982 | Crockford | 424/1.1 |
| 4,331,647 | 5/1982 | Goldenberg | 424/1.1 |
| 4,348,376 | 9/1982 | Goldenberg | 424/1.1 |
| 4,359,457 | 11/1982 | Neville, Jr. | 424/85 |
| 4,361,544 | 11/1982 | Goldenberg | 424/1.1 |
| 4,381,292 | 4/1983 | Bieber | 424/1.1 |
| 4,443,427 | 4/1984 | Reinherz | 424/1.1 |
| 4,454,106 | 6/1984 | Gansow | 424/1.1 |
| 4,472,371 | 9/1984 | Burchiel | 424/1.1 |
| 4,472,509 | 9/1984 | Gansow | 436/548 |
| 4,507,391 | 3/1985 | Pukel | 436/504 |
| 4,522,918 | 6/1985 | Schlom | 435/68 |
| 4,569,788 | 2/1986 | Mulshine | 435/7 |

FOREIGN PATENT DOCUMENTS

WO81/1849 7/1981 PCT Int'l Appl. .

OTHER PUBLICATIONS

Ashall, F. et al., *The Lancet*, Jul. 3, 1982, pp. 1–10.
Herlyn, D. M. et al., *Cancer Research*, 40:717–721 (1980).
Koprowski, H. et al, *Science*, 212:53–55 (1981).
Mattes, M. J. et al, *Proc. Natl. Acad. Sci, USA*, 81:568–572 (1–1984).
Schlom, J. et al., *Proc. Natl. Acad. Sci. USA*, 77(11):6841–6845 (11–1980).
Steplewski, Z. et al, *Cancer Research*, 4:2723–2727 (7–1981).
Stramignoni, D. et al, *Int. J. Cancer*, 31:543–552 (1983).
Thompson, C. H. et al, *British J. Cancer*, 47:595–605, (1983).
Ng, A. K. et al, *J. of Immunology*, 127(2):443–447 (1981).
Ware, J. L. et al, *Cancer Research*, 42(4):1215–1222 (1982) cited in Chem. Abst. 96(21):179218j.

*Primary Examiner*—Margaret Moskowitz
*Attorney, Agent, or Firm*—Silverman, Cass Singer & Winburn, Ltd.

[57] ABSTRACT

A murine monoclonal antibody specific for an antigenic determinant on the surface or in the cytoplasm of human carcinoma cells and tissue. A cell line is provided for producing such specific monoclonal antibodies for the detection, diagnosis, and therapeutic treatment of a plurality of human carcinomas by means of selective labelling of said monoclonal antibodies.

38 Claims, No Drawings

MONOCLONAL ANTIBODY TO A HUMAN CARCINOMA TUMOR ASSOCIATED ANTIGEN

CROSS REFERENCE TO RELATED APPLICATION

This application is a Continuation-In-Part of our prior pending application, Ser. No. 670,328 filed Nov. 9, 1984 and entitled MONOCLONAL ANTIBODY TO A HUMAN CARCINOMA TUMOR ASSOCIATED ANTIGEN, now abandoned.

This invention relates to monoclonal antibodies and particularly, to murine monoclonal antibodies which demonstrate reactivity to a specific antigen on the surface or in the cytoplasm of human carcinoma cells and tissue.

BACKGROUND OF THE INVENTION

The human system involves the production of serum proteins, known as antibodies, by the lymphoid cell series capable of reacting with antigenic determinants which trigger their production. Since the conventional response of the immune system to an antigen with many antigenic determinants is the production of antibodies to each determinant, the antiserum produced is heterologous in nature and polyclonal, or produced by many different cells each producing antibodies to a specific determinant. Antigenic determinants may be referred to as epitopes when more than one occurs on a single molecule and particularly when each elicits an antibody developing, immune response. A single antibody molecule is specific for a unique antigenic determinant or epitope.

Monoclonal antibodies are uniform antibodies directed to a single determinant or epitope on the antigen molecule which may be repeated at several sites of the molecule. Obviously, to produce such monoclonal antibodies in vitro requires selecting a homogeneous antibody having the desired specifications from numerous antibodies elicited in a conventional polyclonal response. The basic technology for in vitro production of homogeneous, highly specific, monoclonal antibodies was developed by Kohler, G. and Milstein, C. (Nature 256:495-497, 1975) known as hybridoma technique. This method involved the immunizing of mice with antigens resulting in the harvesting of antibody-producing cells from those animals, and fusing these antibody-producing cells with a strain of antibody non-producing myeloma cells, e.g. plasma cell tumor cells, to produce hybridomas. These hybridomas are robust cells which have all of the in vitro survival and growth stamina of the myeloma cell line and antibody producing quality of the B lymphocytes with which it was fused. The hybridomas thus produce monoclonal antibodies and may either be cultured in vitro or may be grown as tumors in a host animal. Since each antibody-producing cell produces a single, unique antibody, the monoclonal cultures of hybridomas each produce a homogeneous antibody which may be obtained either from the culture medium of hybridoma cultures grown in vitro or from the cells, injected into the peritoneal cavity of mice producing ascitic fluid, or serum of a hybridoma tumor bearing host animal.

Although the general scheme of hybridoma and monoclonal antibody production is well known at this stage of implementation, great care must be exercised in the separation and maintenance of hybridoma cells in culture. Isolated clones have been known to produce antibodies against a subject antigen which differs from clone to clone since antibodies produced by different cells may react with different antigenic determinants on the same molecule. Adequate testing of the resulting antibody or antibody-containing medium, serum or ascitic fluid is essential. It is necessary to characterize the antibody of each clone which contributes to the complexity of producing monoclonal antibodies which are to be utilized in both diagnostic and therapeutic applications.

In developing a desired monoclonal antibody, one must identify and locate the antigenic determinant which will elicit a specific antibody to bind with it. Or, conversely, develop several hundred hybridoma clones from fusions performed and exhaustively screen them against normal and non-normal tissue and different antigens in identifying and defining that clone which produces the antibody with desired binding specificity. According to this invention the antibody produced detects structural differences on cell surface markers associated with the onset of adenocarcinoma and squamous cell carcinoma, the primary types of carcinoma. The primary object of this invention is to create and maintain hybridomas which produce monoclonal antibodies which will bind with such a particular antigenic determinant to achieve this desired functional specificity.

It is known that monoclonal antibodies may be labeled with a selected variety of labels for desired selective usages in detection, diagnostic assays or even therapeutic applications. In each case, the binding of the labelled monoclonal antibody to the determinant site of the antigen will signal detection or delivery of a particular therapeutic agent to the antigenic determinant on the non-normal cell. A further object of this invention is to provide the specific monoclonal antibody suitably labelled for achieving such desired selective usages thereof.

This invention has particular application to achieving identification of carcinoma cells which occur in the specific diseases of adenocarcinoma and squamous cell carcinoma, the primary forms of carcinoma.

SUMMARY OF THE INVENTION

Murine monoclonal antibodies specific to a unique antigenic determinant on the surface and in the cytoplasm of human neoplastic tissue are produced. The unique antigenic determinant is designated the "KC-4 antigen" which is capable of eliciting an antibody which binds selectively only to neoplastic carcinoma cells and not to normal human tissues. The unique antigen appears in two forms in carcinoma cells of which only the smaller is expressed in the cell membrane. The first is the larger form and appears only in the cytoplasm and has a molecular weight of approximately 490,000 daltons (range of 480,000–510,000). The second form occurs at higher density expression and is found in both the cytoplasm and membrane of carcinoma cells and has a molecular weight of approximately 438,000 daltons (range of 390,000–450,000) determined by subjecting the KC-4 antigen to electrophoresis methodology and comparing movement thereof with marker protein molecules of known molecular weight (Towbin, et al Proc. Natl. Acad. Sci. 76:4350–4354, 1979 and Laemmli, U.K. Nature, 227:680, 1970). The monoclonal antibody, called "KC-4" of the invention has useful application in the areas of diagnosis and medical treatment of a plurality of carcinomas by means of selective labels affixed thereto.

The KC-4 monoclonal antibody is particularly useful in its application to binding with the antigenic determinants on and in carcinoma cells which occur in the specific diseases of adenocarcinoma and squamous cell carcinoma regardless of the human organ of origin.

DESCRIPTION OF THE SPECIFIC EMBODIMENTS

The present invention provides murine monoclonal antibodies specific to a particular antigen on the surface or in the cytoplasm of human carcinoma tissue, such as adenocarcinoma and squamous cell carcinoma. This unique antigen, designated "KC-4 antigen", was developed from human carcinoma tissue involving prostate adenocarcinoma. All monoclonal antibodies having this specificity for the defined "KC-4 antigen" can be referred to as "KC-4".

A Balb/c mouse was innoculated intraperitoneally over a two week period using an initial injection of prostatic adenocarcinoma cells. Two additional injections followed using as an immunogen a crude tumor homegenate from the same tumor. The spleen of the mouse was perfused four days following the additional injections to isolate individual cells. Then, cells of the mouse plasmacytoma cell line, known as Sp2/0-Ag14, were fused with the mouse splenocytes using a modified Kohler and Milstein procedure (Nature 256:495–497, 1975). Fused cells were then cultured for 10–14 days in HAT media to develop cell colonies capable of multiplying in the media. Conditioned media containing the antibody secreted from each colony was removed and screened for specific activity. Media was used to stain normal and prostatic adenocarcinoma tissue. Fused cell colonies exhibiting the desired reactivity were single cloned and further tested on a variety of normal and neoplastic tissues including carcinoma.

The cloning procedure for the selected fused cell colonies, which were KC-4 producing colonies, was preformed in soft agar. Cells were mixed with liquified agarose and the mixture was plated in well plates and allowed to solidify. Then, the plates were incubated and monitored, individual clones being harvested between 10 to 14 days. The individual clones were each screened by immunofluorescent and immunoflouresent staining of human tissue and cell lines. Clones producing the desired antibody were isolated and cloned again in agarose to further assure stability and monoclonal nature.

The monoclonal antibody "KC-4" demonstrates an intense membrane and cytoplasmic antigen distribution on carcinoma cells and gave no specific or positive staining pattern on normal human tissue.

Reactivity of the KC-4 monoclonal antibody on normal and neoplastic human tissues was determined using two methods including biotin/avidin immunoperoxidase and immunofluorescence staining procedures. Both fixed and paraffin embedded tissue, frozen sections, fresh tumor cells and cell lines were used to demonstrate tissue distribution of the specific antigen being identified. A positive result with KC-4 is seen as an intense membrane and/or cytoplasmic stain. A neoplastic specimen showed positive staining of the majority of tumor cells present. No specific reactivity with normal tissue specimens or normal cells has been observed throughout the screening analyses.

One hundred and four different cases of solid tumors or lung, colon, kidney, breast, stomach, prostate, pancreatic, lumph node ductal, and lymphoma different tumor tissues were tested with the KC-4 antibody. All such cases were heat processed, paraffin prepared tissues. Ninety-four percent of these cases (98/104) were positive. All positive staining appeared only on tumor cells while all normal tissue remained unaffected. The six percent false negative staining was attributed to poorly prepared tissue which destroyed rather than preserved KC-4 expression.

Ninety-two different cases of paraffin embedded normal tissue including spinal cord, breast, uterus, thyroid, tongue, prostate, spleen, adrenal, lung, kidney, gall bladder, heart, lumph node, stomach, colon, liver, brain, testes, thymus, and placenta were tested with the KC-4 antibody. All 92 cases were heat processed, paraffin prepared tissues. Only 15.2% (14/92) demonstrated some staining. In all of these positives, the staining was attributed to normally occuring artifacts found in these tissues. The greatest amount of non-specific staining of the normal tissue was in breast, kidney, and stomach tissue. The staining in the breast tissue was found in the alveolar cells of the glands. This is a common finding and is considered to be non-specific on the antibody. The convoluted distal tubules picked up some staining in the kidneys. This is seen with almost all antibodies and is non-specific in origin. Mucous picks up the stain with most antibodies and this is the case with the normal stomach tissue and KC-4. This staining is considered non-specific and artifactual.

Thirty-three different normal tissues from prostate, lung, kidney, liver, lymph node, spleen, colon, thymus, breast, gall bladder and stomach were processed by fresh frozen section and tested with the KC-4 antibody. No heat was used in processing these specimens. Only 3% (1/33) demonstrated any positive staining. It should be noted that frozen tissue sections are more like the fresh tissue than heat processed, formalin fixed, and paraffin embedded tissue. Therefore, the difference is percent positive staining of KC-4 on normal frozen tissue (3%) vesus normal fixed/embedded tissue (15%) is articfactually created in the method of tissue preparation.

Further analyses were conducted on frozen human tumor tissue of colon, prostate, lung, and breast carcinoma with KC-4 antibody staining. One hundred percent of the neoplastic carcinoma tissues were positive with KC-4 i.e., deep cytoplasmic and cell surface specific staining was observed.

The KC-4 antigen molecule was isolated and identified as having two forms. The larger of the forms has an approximate molecular weight of 490,000 daltons (range of 480,000–510,000) and occurs only in the cytoplasm of carcinoma cells. The smaller form has an approximate molecular weight of 438,000 daltons (range of 390,000–450,000) and occurs in both the cytoplasm and the membrane of carcinoma cells. This isolation was accomplished by lysing cells of the HT-17 cell line, derived from a human breast carcinoma, in distilled water at $1 \times 10^8$ cells/ml employing repeated freezing and thawing. The lysates were centrifuged at $100,000 \times g$ to prepare a membrane pellet and a cytoplasm supernatant. The cytoplasm was diluted 1:1 in SDS-PAGE sample buffer. The membranes were dissolved in SDS-PAGE sample buffer. Both samples were heated to 90° for 5 minutes. Subsequently, $23 \times 10^6$ cells equivalent of each sample was run on SDS polyacrylamide (3.5–10% gradient) electrophoresis carried out on a discontinuous vertical slab gel according to a modification of the procedure described in Laemmli, U.K. Nature No. 227,680,1980. The internal molecular weight markers were fibrinogen (340,000), fibronection (440,000), myosin (200,000), beta-galactosidase (116,000), phosphorylase B (92,500), bovine Albumin (66,000), ovalbumin (43,000), carbonic anhydrase (30,000), trypsin inhibitor (20,100), and alpha-lactalbumin (14,000). After electrophoresis, the proteins in the acrylamide slab were electroblotted to a sheet of nitrocellulose according to a modification of the procedures described in Towbin (1979) Proc. Natl. Acad. Sci., 76,4350. The nitrocellulose was then blocked in bovine albumin containing buffer. Monoclonal antibody, KC-4, was then reacted with the nitrocellulose to bind to the specific antigen located on the nitrocellulose. After washing away unbound KC-4 antibody, an anti-mouse immunoglobulin, enzyme conjugate was reacted with the KC-4 antibody bound to the nitrocellulose. After washing away unbound conjugate, enzyme substrate was added and colored bands appear where the KC-4 antigen had migrated.

The "KC-4" monoclonal antibody specifically reactive with the KC-4 antigen was found in two forms. A mouse IgG3 isotype and an IgM as evidenced by its reactivity with a goat anti-mouse IgG3 and IgM antibody and its lack of reactivity with other goat and/or rabbit anti-mouse immunoglobulin isotype specific antibodies.

A sample of both hybrid cell lines capable of producing monoclonal antibodies specific for the KC-4 antigen are on deposit with the American Type Culture Collection, 12301 Parklawn Drive, Rockville, Md. 20852, and are assigned the Nos. 8709 (IgG3) and HB 8710 (IgM).

The availability of homogeneous, highly specific monoclonal antibodies is an especially valuable tool for diagnostic and therapeutic applications in the detection and treatment of human carcinomas.

As a diagnostic tool, the KC-4 monoclonal antibodies can be brought into contact with a biological sample of human carcinoma cells derived from human neoplasia. Immunological complexes derived between the monoclonal antibody and carcinoma cells in the biological sample can be detected, said complexed cells being monoclonal antibody and human neoplastic cells.

This methodology can also be applied to detect and measure the KC-4 antigen in serum or other liquid biological samples derived from human patients suspected of having human carcinoma or related tumors.

Further, said complexes can be detected by contacting that biological sample of the human carcinoma with a second antibody capable of binding to the KC-4 monoclonal antibody. Said second antibody is labeled with a detectible compound (detector group) selected to enable said complexes to be labelled with said detectible compound when said second antibody binds to said monoclonal antibody specific for the KC-4 antigen. The resulting labelled complex can then be detected. For diagnostic applications, said detector group can be selected from a fluorescent compound, an enzyme which produces an absorptive or fluorescent detector group when reacted with a specific substrate, radioactive element, or an electron dense compound. (Goldman, Morris Fluorescent Antibody Methods. Academic Press, New York, 1968; Yoshitake, S. et al. Scand. J. Immunol. 10:1–6, 1979; Hunter, W. M. & Greenwood, F. C. Preparation of iodine 131 labelled growth hormone of high specific activity. Nature, 194, 495,1962).

Detector groups suitable for this function include fluorescent compounds such as fluorescein, rhodamine, phycoerythrin, cyamine dyes, and any other compound emiting fluorescene energy. Other categories of detector groups include enzyme substrate products which form fluorescent compounds such as N-methylumbelliferone-B-D-galactosidase or absorptive compounds as DAB (di-aminobenzidine). There are many others in these categories. Radioactive elements which are suitable as detector groups include Iodine-125, Iodine-131, Indium-111, Bismuth-210, and several others of which these are presently the most often used compounds. Electron dense detector groups would include such compounds as gold and ferric chloride, as presently known. Although this approach is predominantly employed on in vitro diagnostic applications it does not exclude in vivo diagnostic or therapeutic application of similarly labeled KC-4 antibody.

The KC-4 monoclonal antibody can be used for detecting carcinoma in a human patient. In this application, KC-4 monoclonal antibody is treated to develop a label thereon capable of producing a detectible signal and infusing said monoclonal antibody into the patient thereby labeling said tumor when the monoclonal antibody binds to the antigenic determinant thereof. Such a detectible label can comprise a radioactive element, a fluorescent compound or other suitable detectible label or compound. This approach is equally suited for in vitro diagnostic detection of carcinoma cells on tissues which has been frozen, fixed, or fixed and heat processed with paraffin embedding. Additional in vitro applications include the radioimmunoassay or radioimmunometric assay or enzyme immunoassay or nephlemetric detection of KC-4 antigen is serum, plasma, or other liquid based biological samples such as cerebral spinal fluid, urine, and sputum.

For therapeutic treatment with the intent of inhibiting or eliminating human carcinoma in a patient suspected of having such a tumor, the KC-4 monoclonal antibody or KC-4 conjugated with a suitable toxic agent can be injected into the patient in a controlled protocol of administrations whereby said monoclonal antibody or monoclonal antibody—toxic agent—conjugate can bind to the tumor and effect tumor cell death. Examples of such a toxic agent can be a chemotherapeutic agent, a photo-activated toxic agent or radioactive agent. Examples of such a radioactive agent are Iodine-125, or Bismith-210. Examples of a chemotherapeutic agent would include the alpha chain or A-chain ricin, diphtheria, or whole molecules, cytoxin adriamycin, methyltrexate, and platinium compounds, such as cisplatin. Examples of photo activated toxic agents include infrared dyes, such as in the cyanine family.

Modifications obvious to one with ordinary skill in the art may be made without departing from the scope of the present invention. Various features of the invention are set forth in the claims which follow.

What is claimed is:

1. A cell line produced by a hybridoma technique which produces a monoclonal antibody which specifically binds to KC-4 antigen of human carcinoma cells.

2. The cell line according to claim 1 wherein said monoclonal antibody-producing cells are derived from the murine genus.

3. The cell line according to claim 1 wherein said monoclonal antibody-producing cells are derived from mouse spleen cells.

4. The cell line according to claim 3 in which said cells are derived from mice immunized with human carcinoma cells.

5. The cell line according to claim 1 which was derived from a fusion with mouse myeloma cells.

6. The cell line of claim 3 in which the antibody-producing cells were derived from Balb/c mice.

7. The cell line of claim 1 in which said KC-4 antigen is sited on the surface or in the cytoplasm of the human carcinomas and the antigen further is characterized as having a molecular weight in the range of 390,000–450,000 daltons and the antigen is further characterized by expression in a larger form found only in the cytoplasm and having a molecular weight in the range of 480,000–510,000 daltons as determined by electrophoresis methodology applied to the antigen and comparing the antigen movement with that of known marker proteins of known molecular weights.

8. The cell line of claim 7 wherein said antigen has an approximate molecular weight of 490,000 daltons.

9. The cell line of claim 7 wherein said smaller form has an approximate molecular weight of 438,000 daltons.

10. A cell line produced by a hybridoma technique having the essential characteristics of the samples on deposit with the American Type Culture Collection Nos. HB 8709 producing mouse IgG3 isotype antibody to KC-4 antigen or HB 8710 producing mouse IgM isotype antibody to KC-4 antigen.

11. A monoclonal antibody which specifically binds to an antigen on the surface or in the cytoplasm of human carcinoma tissue, said antigen being further characterized in that
   a. It has a molecular weight in the range of 380,000–450,000 as determined by carrying out electrophoresis on the antigen and comparing its movement with that of marker proteins of known molecular weight,
   b. It may be expressed in a slightly larger form found only in the cytoplasm and it has a molecular weight in the range of 480,000–510,000 daltons as determined by said electrophoresis method, and
   c. It is essentially undetectible on normal human tissue.

12. The monoclonal antibody of claim 11 having mouse isotype IgG3 or IgM which is produced by the hybrid cell line having the essential characteristics of ATCC HB 8709 or ATCC HB 8710 respectively.

13. The antibody of claim 11 wherein said antigen has an approximate molecular weight of 490,000 daltons.

14. The antibody of claim 11 wherein said smaller form has an approximate molecular weight of 438,000 daltons.

15. A method of detecting human carcinoma cells contained in a biological sample, said method comprising contacting said biological sample with the monoclonal antibody of claim 11, for a time and under conditions sufficient for the formation of immunological complexes between said monoclonal antibody and said cells contained in said biological samples and then detecting immunological complexes resulting from said contact between said monoclonal antibody and cells in said sample, the cells complexed with said antibody being human carcinoma cells.

16. The method of claim 11 including a step of obtaining said biological sample from a human patient suspected of having a carcinoma tumor.

17. The method of claim 16 wherein said detecting of said complexes comprises contacting said biological sample with a second antibody capable of binding to said monoclonal antibody, said second antibody being labelled with a detectible compound such that said complexes are labelled with said detectible compound when said second antibody binds to said monoclonal antibody, and detecting said labelling complexes.

18. The method of claim 17 wherein said detectible compound is a fluorescent compound.

19. The method of claim 17 wherein said detectible compound is produced by an enzyme bound to said second antibody.

20. The method of claim 17 wherein said detectible compound is a radioactive element.

21. The method of claim 17 wherein said detectible compound is an electron dense element.

22. A murine monoclonal antibody of the mouse IgG3 or IgM isotype which specifically binds to KC-4 antigen.

23. The antibody of claim 22 conjugated to a detectible label.

24. The antibody of claim 23 wherein said label is a fluorescent compound, an enzyme label, a radioactive element, or an electron dense element.

25. A murine monoclonal antibody of the mouse IgG3 or IgM isotype, which specifically binds to KC-4 antigen, conjugated to a chemotherapeutic, photoactivated toxic or radioactive agent.

26. A method of detecting a human carcinoma tumor in a patient suspected of having said tumor, said method comprising infusing a monoclonal antibody, which specifically binds to KC-4 antigen, derivitized with a radioactive element into said patient for a time and under conditions sufficient for the formation of immunological complexes between said monoclonal antibody and said tumor, thereby labelling said tumor with the derivitized monoclonal antibody thereby detecting said tumor.

27. A method of inhibiting or killing tumor cells of a human carcinoma tumor in a patient suspected of having said tumor, said method comprising infusing a monoclonal antibody or a monoclonal antibody-toxic agent conjugate, which specifically binds to KC-4 antigen, into said patient for a time and under conditions sufficient for the formation of immunological complexes between said antibody-toxic agent conjugate and said tumor and causing tumor cell death.

28. The method of claim 27 wherein said monoclonal antibody-toxic agent conjugate is administered to said patient in a series of more than one infusion.

29. The method of claim 27 wherein said toxic agent is a chemotherapeutic agent.

30. The method of claim 27 wherein said toxic agent is a photoactivated toxic agent.

31. The method of claim 27 wherein said toxic agent is a radioactive agent.

32. The method of claim 31 wherein said radioactive agent is Iodine 125 or Bismuth 210.

33. The method of claim 27 wherein said toxic agent lyses the tumor cell with which the antibody binds.

34. The method of claim 33 in which said toxic agent lyses said cells in vivo.

35. A method of detecting the KC-4 antigen of KC-4 antigen-containing human carcinoma cells in a biological sample, said method comprising contacting said biological sample with a monoclonal antibody, which specifically binds to KC-4 antigen, coated on fluorescent microspheres under conditions to permit an immunological reaction and satelliting of the carcinoma cells and detecting the immunological complexes.

36. A method as described in claim 35 in which said KC-4 antigen is on the surface of the carcinoma cell.

37. A method of detecting KC-4 antigen contained in a biological sample comprising contacting said sample with a monoclonal antibody, which specifically binds to KC-4 antigen, coupled to a label selected from the group comprising a radioactive element, and an enzyme label capable of producing a substrate reaction detectible product, for a time and under conditions sufficient for the formation of immulogical complexes between said monoclonal antibody and said antigen and detecting the immunological complexes.

38. A method of detecting the KC-4 antigen of KC-4 antigen-containing human carcinoma cells in a biological sample, said method comprising contacting said sample with microspheres coated with a monoclonal antibody, which specifically binds to KC-4 antigen, under conditions to permit immunological reaction between said KC-4 antigen-containing human carcinoma cells and said monoclonal antibody so as to form an agglutinate, contacting the agglutinate with a second antibody which binds to said monoclonal antibody and is coupled to a detectable label under conditions to permit an immunological reaction between said second antibody and said agglutinate, and detecting the label present on said labeled agglutinate.

* * * * *

UNITED STATES PATENT AND TRADEMARK OFFICE
CERTIFICATE OF CORRECTION

PATENT NO. : 4,708,930

DATED : November 24, 1987

INVENTOR(S) : Kenneth H. Kortright and David E. Hofheinz

It is certified that error appears in the above-identified patent and that said Letters Patent are hereby corrected as shown below:

Claim 7, lines 2-3, change "the human carcinomas" to --said human carcinoma cells--.

Claim 8, line 1, between "wherein" and "said" insert --said larger form of--.

Claim 11, line 6, between "450,000" and "as" insert --daltons--.

Claim 12, line 1, change "The" to --A--.

Claim 13, line 1, between "wherein" and "said" insert --said larger form of--.

Claim 22, line 3, change "antigen." to --antigen, expressed on the surface of or in the cytoplasm of human carcinoma cells.--.

Claim 26, line 8, change "thereby labelling said tumor" to --and detecting said radiolabelled tumor--.

Claim 35, line 6, between "microspheres" and "under" insert --for a time and--.

Claim 35, lines 6-7, change "to permit an immunological reaction and satelliting of the carcinoma cells" to --sufficient for binding of said antibody-coated microspheres to said carcinoma cells for form immunological complexes--.

Claim 38, line 11, delete "detectible" and insert --detectable--.

UNITED STATES PATENT AND TRADEMARK OFFICE
CERTIFICATE OF CORRECTION

PATENT NO. : 4,708,930
DATED : November 24, 1987
INVENTOR(S) : Kenneth H. Kortright and David E. Hofheinz It is certified that error appears in the above-identified patent and that said Letters Patent is hereby corrected as shown below:

Claim 38, line 14, delete "labeled".

Signed and Sealed this

Twenty-ninth Day of March, 1988

Attest:

DONALD J. QUIGG

*Attesting Officer*　　　　*Commissioner of Patents and Trademarks*

UNITED STATES PATENT AND TRADEMARK OFFICE
CERTIFICATE OF CORRECTION

PATENT NO. : 4,708,930

DATED : November 24, 1987

INVENTOR(S) : Kenneth H. Kortright, et al.

It is certified that error appears in the above-identified patent and that said Letters Patent is hereby corrected as shown below:

Claim 16, line 1, change "11" to --15--.

Signed and Sealed this

Twenty-ninth Day of November, 1988

Attest:

DONALD J. QUIGG

Attesting Officer

Commissioner of Patents and Trademarks